United States Patent [19]

Sanderson

[11] 4,400,376

[45] Aug. 23, 1983

[54] IMMUNOLOGICAL PREPARATIONS

[75] Inventor: Arnold R. Sanderson, East Grinstead, England

[73] Assignee: National Research Development Corporation, London, England

[21] Appl. No.: 224,565

[22] PCT Filed: Mar. 27, 1980

[86] PCT No.: PCT/GB80/00055

§ 371 Date: Nov. 17, 1980

§ 102(e) Date: Nov. 17, 1980

[87] PCT Pub. No.: WO80/01986

PCT Pub. Date: Oct. 2, 1980

[30] Foreign Application Priority Data

Mar. 27, 1979 [GB] United Kingdom ................. 7910639

[51] Int. Cl.³ .................. A61K 39/00; A61K 39/385; C07G 7/00
[52] U.S. Cl. ................................. 424/88; 260/112 R; 424/85; 424/86; 424/87; 424/89; 424/91; 424/92; 436/543
[58] Field of Search .......................... 424/8, 12, 85-89, 424/91, 92, 177; 260/112 R; 436/543

[56] References Cited

FOREIGN PATENT DOCUMENTS 1945251 3/1971 Fed. Rep. of Germany .
2266518 11/1978 France .
2004744 4/1979 United Kingdom .

OTHER PUBLICATIONS

Fujimoto, J. of Immunol. vol. 111, 1973, pp. 1093-1100.
Gooding, The J. Exptl. Med., vol. 140, 1974, pp. 61-78.
Klaus, Immunology, vol. 34, 1978, pp. 643-653.
Henning, Nature, vol. 263, Oct. 21, 1976, pp. 689-691.
Garrido, Nature, vol. 261, Jun. 24, 1976, pp. 705-707.
Parham, Nature, vol. 276, Nov. 23, 1978, pp. 397-399.
Sanderson, Nature, vol. 269, Sep. 29, 1977, pp. 414-417.

*Primary Examiner*—Anna P. Fagelson
*Attorney, Agent, or Firm*—Oblon, Fisher, Spivak, McClelland & Maier

[57] ABSTRACT

An immunological preparation of an antigenic material in combination with a major histocompatibility complex antigen, which is itself in the form of complex with a protein with which it is normally associated in nature or with a modified form of such protein which retains the epitope thereof intact, said antigenic material being attached to the protein of the complex through antibody to that protein, is disclosed as being useful for the production of an immunogenic response in human or veterinary use.

28 Claims, No Drawings

IMMUNOLOGICAL PREPARATIONS

This invention relates to immunological preparations, particularly those containing antigenic materials.

Immunisation, for example against infectious diseases, is widely used in both a human and a veterinary context. It is often the case, however, that the antigenic material contained in the immunological preparation is not as immunogenic as could be desired, necessitating the use of a plurality of injections of the preparation. As an alternative, or in addition to the use of repeated injections, an adjuvant may be incorporated in the immunological preparation in order to increase the immune response provoked by the antigenic material. However, the effective adjuvants at present available, for example Freund's incomplete and complete adjuvants, have disadvantages particularly for human use. For some time, therefore, attempts have been made to discover new forms of adjuvant which would simplify immunization procedures and reduce the amounts of antigenic material required or amplify the response to a given quantity of antigenic material. Such an effect is applicable not only for protective immunization but also for the production of therapeutic or diagnostic immunological and serological reagents.

In U.K. Pat. Application No. 7838177 there is described and claimed a novel form of immunologically active preparation based upon the discovery that members of a group of naturally occurring substances have the effect of increasing the immunogenicity of antigenic materials when administered in combination therewith. Such preparations comprise an antigenic material in combination with an MHC (Major Histocompatibility Complex) antigen.

I have now developed a new approach to the production of such combinations of antigenic material with MHC antigen which has particular advantages as compared with the modes of preparation described in U.K. Patent Application No. 7838177.

Accordingly the present invention comprises an antigenic material in combination with an MHC antigen which is itself in the form of a complex with a protein with which it is normally associated in nature, said antigenic material being attached to the protein of the complex through antibody to that protein.

MHC antigens have been found in all animal species (including man) where they have been sought, being carried on the surface of nucleated cells of tissues, and constitute a particularly polymorphic system within any species. Therefore, although it is necessary in order for the MHC antigen to enhance the immunogenicity of the antigen material with which it is combined, that the MHC antigen should contain an antigenic determinant or determinants foreign to the recipient, the extreme polymorphism of these MHC antigens is generally sufficient to ensure that this is the case between one member of a species and another, except in the extreme case of members of a species which are genetically identical. The MHC antigen may therefore be from either the same species or another species, for example a phylogenetically similar species such as a primate in the case of preparations for human administration. MHC antigen from the same species may often be preferred, however, unless there are reasons, particularly an enhancement of effect, for using MHC antigen from another species.

One major group of MHC antigens to which the present invention is applicable comprises the HLA antigens which are found in man and the analogous antigens of other species. Such MHC antigens are referred to by many workers as SD (Serologically Determined) antigens. A second group of MHC antigens of some interest which may be distinguished from these Serologically Determined MHC antigens, are those antigens such as the Ia antigens of mice and their equivalents in man (DRW) and other animal species. Examples of the MHC antigens analogous to HLA in other species are RLA in rabbits and H-2 in mice, etc. The MHC antigens of a combination according to the present invention may be of various specificities. Moreover, they may comprise not only the whole molecule which occurs in nature but also a portion thereof which retains the epitope intact, for example such derivatives as the papain-solubilised MHC antigens.

In their natural form, MHC antigens are normally bound to a protein molecule, for example HLA and the equivalent MHC antigens of other non-human species being bound to B2-microglobulin (B2M) of the appropriate species. The nature of the binding between the two molecules in such a normal association of MHC antigen and protein is not yet known for any species, although present indications are that it is not of the form of a covalent bond. However, the bonding is strong enough so that in several species, including man, B2M is co-isolated with MHC antigen under normal circumstances. It will be appreciated, therefore, that the reference made hereinbefore to "an MHC antigen which is itself in the form of a complex with a protein with which it is normally associated in nature" refers to this type of protein and not to a protein with which the MHC antigen may be associated only under certain particular circumstances, for example on occurrence of a pathological condition. Moreover, the B2M or other similar protein component of such a complex may be the whole protein or a suitable modification thereof which retains the epitope since it is the epitope which is necessary for attachment of the antibody and thus the antigenic material to the complex. Thus, the protein, for example a B2-microglobulin, present in a combination according to the present invention may be not only the whole protein found in nature but also a portion thereof which retains the epitope intact.

The present invention derives from the appreciation that significant advantages accrue from attaching the antigen whose immune response it is desired to increase to an antibody against the protein which is in turn attached to the protein of the MHC-protein complex. Such a procedure enables the antigenic material and the MHC-protein complex to be combined through an immunological rather than a chemical reaction with all the advantages which this implies by way of specificity, lack of de-naturation, and consequent high yield etc. In particular, it is possible by this method to obtain a product of a very high state of purity.

For the sake of convenience only, further discussion of the preparation of a combination as defined above will be presented in terms of a combination of the type antigenic material/anti-B2M/B2M/MHC although it will be appreciated that the discussion is generally applicable to combinations incorporating other than B2M proteins.

The antibody which forms a vital part of a combination according to the present invention is often of the IgG type but this is not necessarily always the case. It is usually desirable that the MHC/B2M complex and thus the antibody thereto, is specific for the intended human, mammalian or avian recipient of the immunological preparation. Commonly, therefore, a complex of HLA or the equivalent bovine, horse, pig, sheep, chicken etc., LA with the appropriate species B2M is used. However, although it is the case, for example, that for the treatment of cattle and pigs bovine LA and porcine LA are preferred as the MHC antigen, there may in some instances be an advantage in using the MHC antigen of a closely related species in combination with the B2M of that species so that, for example, the use of bovine LA in pigs and of porcine LA in cattle may be considered in addition to the more usual intraspecies usage.

Production of the antibody is conveniently effected through one of the standard immunological techniques which are described in the literature of this art. A preferred method involves the use of B2M of the appropriate species as the antigen in the established techniques of monoclonal antibody production. This technique involves the immunisation of a suitable animal host, for example a mouse or a rat of a suitable strain for the cell line used, with the B2M protein followed by fusion of spleen or other immunocyte cells from the animal with cells of a suitable cell line, such as the mouse P3-X63-Ag8 or NS1/1-Ag4-1 and the rat 21ORC Y3-Ag 1.2.3 cell lines of Milstein, to produce a hybrid cell line capable of anti-B2M production. The hybrid cells may then conveniently be inoculated into the appropriate animal host to induce myeloma growth therein, and the antibodies subsequently isolated from serum or ascites. As B2M is an immuno-dominant species it is possible simply to use lymphocytes as a source thereof for injection into the animal host. A source of isolated B2M is not therefore necessary for this purpose. Such material is, however, available in the use of human B2M from the urine of patients with renal failure and is of value in purification of the anti-B2M prepared in vivo since such purification may conveniently be effected by passing the material obtained, for example from serum or ascites, through a column of B2M coupled to a suitable support material, for example a Sepharose such as that marketed under the designation S4B. The antibody immunologically bound to the immoblised B2M may conveniently be eluted with a suitable aqueous acidic medium, for example aqueous glycine hydrochloride. An alternative technique for producing the antibody from the hydrid cells comprises their culture in vitro which will in general give a purer product but may present more problems with regard to the production of a significant quantity of antibody.

It is not necessary for the combination to contain the whole of the antibody and, if desired, the antibody obtained by the procedures as described above may be treated by conventional methods to separate a sub-fraction thereof which is combined with the antigenic material rather than the whole antibody. The antibody, for example anti-B2M, present in a combination according to the present invention may thus be the whole antibody or an active fragment thereof. Thus, the F(ab')$_2$ fragment or particularly the Fab fragment may be used, these being obtained, for example, by pepsin and papain hydrolysis, respectively.

As regards the antigenic material, the present invention is widely applicable to a whole variety of antigenic materials which are of use in vaccines or in other contexts, for example in therapeutic or diagnostic immunological and serological reagents. The term "antigenic material" as used herein thus covers any substance that will elicit a specific immune response when formulated in combination with an MHC antigen, and includes antigenic determinants such as peptides (small or large), oligo or polysaccharides, alloepitopes, haptens and the like.

In the context of vaccines for human administration a variety of microbial antigens may be used as the antigenic material. Examples include bacterial antigens, for instance toxins such as Staphylococcus enterotoxin and particularly toxoids such as diphtheria and tetanus toxoid as well as antigens useful in the treatment of conditions such as caries, and viral antigens such as those derived from the influenza and the rabies viruses. The invention is also of interest, however, in relation to vaccines against other forms of pathogen such as protozoa, for example in the treatment of schizotrypanosomiasis, and fungi and also in relation to the field of both human and animal contraception, for example in vaccination against HCG when a hormone peptide is used as the antigenic material, as well as in the immunotherapy of cancer when a tumour specific antigen may be used as the antigenic material. The invention is also of considerable interest and of similar wide applicability in the context of veterinary vaccines for both mammalium and avian administration, for example in the treatment of the viral foot and mouth disease in cattle and pigs.

The antigenic material is conveniently attached to the whole anti-B2M or a fragment thereof by means of a covalent bond. Various techniques are described in the literature for attaching antigens or haptens to proteins and these usually include the use of some form of coupling agent, for example agents such as chromic chloride, divinyl sulphone, cyanogen bromide, bis-diazotized benzidine (BDB) and especially glutaraldehyde, tannic acid and carbodiimides, for example 1-ethyl-3-(3-dimethylaminopropyl)carbodiimide hydrochloride (EDC). One method which has recently attracted some interest is that based upon a procedure described by Kitagawa and Aikawa in the Journal of Biochemistry, 1976, 79, 233, which involves the use of a heterobifunctional coupler or cross-linking agent for use with proteins. Such a coupler contains two different coupling groups which react with different types of functional groups; in the present case, one which will bond to the antigenic material and a different group which will bond to the antibody.

An example of such a heterobifunctional coupler which has been used with some success is N-(m-maleimidobenzoyloxy)succinimide (MBS). This coupler will couple with free amino groups through active ester acylation by the m-maleimido-benzoyl groups and also with sulphydryl groups, for example of cysteine, by addition at the double bond of the maleimido group. For the sake of simplicity the symbol MBS has also been used hereinafter in identifying products linked through the use of this reagent although such products will, or course, only contain a residue of the reagent. Conveniently, the N-(M-maleimidobenzoyloxy)succinimide is coupled first to the antibody through free amino groups therein, the antibody not containing sulphydryl groups. Although such coupling may reduce the antibody activity, the extent of this reduction is not generally sufficient to have any substantial effect upon the subsequent anti-B2M/B2M coupling. The MBS/anti-B2M complex may then be treated with the antigenic material to effect combination therewith through reaction of the MBS moiety with sulphydryl groups naturally present in the antigenic material or inserted therein for this purpose. The formation of antibody not containing sulphydryl groups will often similarly require modification of the natural antibody by treatment with a reagent such as N-ethyl maleimide to block sulphydryl groups present therein.) It will be appreciated from the foregoing that the antigenic material/anti-B2M combination is a key intermediate in the formation of the final combination as described above.

Accordingly, the present invention further comprises an antigenic material in combination with antibody as defined above, for example anti-B2M.

The combination of antigenic material and anti-B2M may be purified simply by gel filtration on a material such as Sephadex G200 to effect a fractionation on the basis of molecular weight. However, a preferred procedure employs, as an initial purification step, the passage of the mixture obtained from the reaction of antigenic material and antibody over an immobilised solid phase to which B2M is attached. This solid phase may comprise one of a variety of forms of polymeric material suitable as the basis of an immunoadsorbent. Such materials are described in the literature in relation to gel filtration chromatography of immunoglobulins and include carbohydrate materials based upon dextran, agar or agarose and also polyacrylamide based materials, cross-linking conveniently being used to impart the required degree of exclusion of molecules dependent upon size and shape. Examples of such materials are marketed under the trade name Sepharose (agarose based), Sephadex (dextran based) and Sephacryl (polyacrylamide based). The dextran material marketed under the trade name Sepharose 4B has, for example, been found to be very suitable. The B2M may be attached to the solid phase through the use of one of the several methods described in the literature by which proteins or other materials may be attached to these insoluble solid phase supports. The chemical reactions described effect covalent bond attachment, but by a non-denaturing methodology so that destruction of the attached labile substances is minimised. Examples of suitable linking agents among such agents described above are glutaraldehyde and particularly cyanogen bromide.

The use of such a B2M column enables unreacted antigenic material (which is often used in excess to effect optimum reaction of the anti-B2M) and any other materials not possessing the ability to bind immunologically to B2M to be separated from the bound antigenic material/anti-B2M combination by eluting the column with a suitable eluant, for example a suitable irrelevant protein solution such as 10% v/v foetal calf serum in phosphate buffered saline. The required combination of antigenic material and anti-B2M is then eluted from the column, together with any unreacted anti-B2M in the form used in the original reaction, for example MBS/anti-B2M, by the use of a further suitable eluant. Such second eluant may be a suitable acidic medium such as a 0.5% v/v aqueous acetic acid solution, or a solution of a chaotropic agent, for example of lithium chloride or iodide or of ammonium thiocyanate at neutral pH.

The initial immunosorbent purification step is conveniently followed by a gel filtration step to effect a separation on the basis of molecular weight. Broadly similar types of solid phase may be used in this step to those used in the previous one but best results are obtained in this instance with materials such as those marketed under the trade names Sephadex G-200 and Sephacryl S-300. In a preferred aspect of this purification procedure, an acidic medium is used for the final elution of the immunosorbent column. The acidic eluate may then conveniently be passed directly from the immunosorbent column to the gel filtration column. This latter column may conveniently be made up and equilibrated in a medium such as phosphate buffered saline which is then also used to elute both the immunosorbent and gel filtration columns in series. The amount of acidic medium used to elute the former column usually does not need to exceed its bed volume and on the second column the acidic eluate is rapidly separated into its acid and protein components which differ widely in molecular weight. Further elution with a medium such as phosphate buffered saline will continue the separation according to molecular weight and result in elution from the latter column of antigenic material/anti-B2M followed by anti-B2M, for example as MBS/anti-B2M, and finally by the acid, for example acetic acid. This procedure results in a rapid separation giving a recovery of the desired antigenic material/anti-B2M combination in purified form with its constituent components having been minimally exposed to denaturing conditions.

The final step in the preparation of the active component of immunological preparations according to the present invention conveniently consists of combining the antigenic material/anti-B2M combination with a B2M-MHC complex. The MHC-B2M complex required may conveniently be obtained from natural sources using one of the procedures for doing this which are described in the literature. The HLA antigens, for example, may conveniently be obtained from solubilised human spleens or by extraction of the membranes of human lymphoblastoid cells cultured in a suitable medium to provide sufficient quantities thereof for extraction. Alternatively, a human non-lymphoid cell line may be used as the source. Conveniently, however, the HLA-B2M complex may advantageously be purified by use of some of the anti-B2M which has been prepared. Thus a column of the anti-B2M coupled to a suitable support material, for example a Sepharose such as that marketed under the designation S4B, may be used and the HLA-B2M complex passed down this column, when it will be retained on the column by attachment to the anti-B2M. Elution with free B2M, not associated with HLA, will then competitively displace the HLA-B2M complex from the column in purified form. Conveniently the B2M may then also be recovered from the column, for example by elution with a suitable aqueous acidic medium such as aqueous glycine hydrochloride, and the column may be restored to a state ready for further repeated use by washing, for example with phosphate buffered saline. Following elution of the HLA-B2M not associated with HLA, the two materials may be separated by gel filtration and the recovered B2M used again.

Coupling of the antigenic material/anti-B2M combination with the B2M-MHC complex may usually be achieved by simple admixture in an appropriate aqueous medium, for example in phosphate buffered saline. This is a simple procedure and, indeed, it may be possible to carry it out just prior to administration of the resulting antigenic material/anti-B2M/B2M/MHC combination. However, in order to restrict coupling to that occurring by an immunological route with the substantial avoidance of chemical coupling, it is possible if desired to block sulphydryl groups in the MHC antigen, for example by the use of N-ethyl maleimide, to prevent binding to these through any residual activity resulting from the coupling agent used in effecting the combination of antigenic material and anti-B2M.

It will be appreciated that the present invention further includes an immunologically active preparation for human or veterinary use comprising an antigenic material in combination with an MHC antigen which is itself in the form of a complex with a protein with which it is normally associated in nature, said antigenic material being attached to the protein of the complex through antibody thereto, together with a physiologically acceptable diluent or carrier.

The amounts of antigenic material incorporated as the immunologically effective agent to provide pharmaceutical preparations according to the present invention may be similar to those used in existing vaccines incorporating such material, but it may be possible in view of the increased immunogenicity to reduce these amounts. Similarly, although additional adjuvants may be incorporated into the preparations, this may likewise be unnecessary. The proportion of MHC antigen to antigenic material may be varied according to the particular circumstances. However, as a guide it may be indicated that in primates three dosages containing about 10, 10 and 5 micrograms of HLA have proved effective and that broadly similar unit dosage levels are generally applicable in humans, for example in the range from 5 to 100 micrograms, particularly from 10 to 50 micrograms, for example about 25 micrograms. A similar basis may be used for veterinary applications with due consideration for variation in body weight.

In other respects, the preparations may be formulated in a similar manner to conventional vaccines, for example in a medium such as isotonic saline, and may be administered similarly, often by a parenteral route, for example intravenously, intramuscularly or subcutaneously.

The present invention thus includes a method for the immunization of a mammal or a bird which comprises administering thereto as an immunologically effective agent an antigenic material in combination with an MHC antigen which is itself in the form of a complex with a protein with which it is normally associated in nature, said antigenic material being attached to the protein of the complex through antibody to that protein.

It should be noted that the HLA antigens, which were originally designated in the literature as Human Lymphocyte Antigens, have more recently been designated by some workers as Human Lymphocyte System A antigens.

This invention is illustrated by the following Examples, a general procedure being described in Examples 1 and 2 and a specific preparation relating to the antigenic material ovalbumin in Examples 3 and 4.

EXAMPLES (Gel filtration and immunosorbent columns are run at room temperatures under peristaltic pumping so as to achieve optimal resolution as defined by the manufacturer.)

EXAMPLE 1

PREPARATION OF ANTIGENIC MATERIAL/ANTI-B2M COMBINATION (a) Preparation of anti-B2M Using the general procedure of Köhler and Milstein (European Journal of Immunology, 1976, 6, 511), a mouse hybridoma is obtained by the fusion of spleen cells from a BALB/c mouse immunised with human B2M, together with the cells of the mouse cell line NS1/1-Ag4-1. During the isolation of the desired clone, hybridoma cells producing anti-B2M antibody are identified by the ability of culture supernatants to bind to the wells of a plastic plate previously coated with pure B2M. Thus, to wells of the plate is first added 50 $\mu$l of a solution of pure B2M at 10-40 $\mu$g protein per ml of phosphate-buffered saline. Following incubation of the covered plate at 37° C. for 1 hour, unadsorbed protein is aspirated and the wells washed thrice with 100 $\mu$l of a solution containing 10% v/v foetal calf serum. Plates may then be stored covered at 4° C. until required. In the assay an aliquot of 25 $\mu$l of culture supernatant is incubated in a well for 1 hour at 37° C. Following washing thrice with 10% v/v foetal calf serum, attachment of mouse immunoglobulin having anti-B2M activity is revealed by the ability of the plate well to bind immunopurified radio-iodinated sheep anti-mouse immunoglobulin [The latter reagent is prepared by immunising sheep with DEAE-cellulose purified mouse IgG. The specific antibody in the serum of immunised animals is purified on a column of mouse IgG prepared by the cyanogen bromide technique (March et al, Analytical Biochemistry, 1971, 60, 149), eluting with 0.1 M-glycine hydrochloride pH 3.0, and immediately neutralising the eluted protein.] Having identified cultures which are actively secreting antibody to B2M, the cells are cloned to homogenity using the "limit dilution" protocol defined by Köhler and Milstein. Cells thus cloned may be preserved in liquid nitrogen using established methodology. When quantities of anti-B2M are required, ampoules of frozen anti-B2M producing hybridoma cells are thawed from liquid nitrogen and about $3 \times 10^6$ cells are injected subcutaneously into BALB/c mice. Serum from such mice soon shows a high titre of monoclonal mouse antibody. Specific antibody is isolated from the serum by use of an immunosorbent column of pure human B2M by the following protocol. B2M is isolated from the urine of patients with renal disease following Berggard and Bearn, Journal of Biological Chemistry 1968, 243, 4095. The purified protein is covalently attached to Sepharose-4B by the cyanogen bromide technique (March et al., ibid) at a final concentration of about 4 mg/ml. Antibody is eluted from the column with 0.1 M glycine hydrochloride at pH 3 or using 0.5% v/v aqueous acetic acid. The eluted protein is immediately neutralised with tris(2-amino-2-hydroxymethylpropane 1,3-diol) base and stored frozen at $-20°$ C. until required. Characterisation of the antibody by SDS-gels or isoelectric focusing establishes its monoclonality.

(b) Fab fragment of antibody

Antibody protein at 10 mg/ml in aqueous solution is incubated with 3% by weight of crystalline papain in 0.01 M-cysteine at pH 7 for 16 hours at 37° C. The Fab fragment is isolated using a similar column of Sepharose 4B-B2M as described above for purification of the intact antibody. In this way only Fab fragments which have retained B2M-binding activity are selected. Elution is with 0.5% v/v acetic acid followed by immediate neutralisation and storage of the Fab protein at $-20°$ C.

(c) F(ab')₂ fragment of antibody

Antibody protein in aqueous solution is incubated with 10% of its weight of crystalline pepsin at pH 4 and 37° C. for 20 hours. The F(ab')₂ fragment is isolated on a column of Sepharose 4B-B2M exactly as described above for the Fab fragment and with the same elution procedure.

(It has been established in small scale trials that the Fab and F(ab')₂ fragments may be repeatedly absorbed to and eluted from Sepharose 4B-B2M columns without undergoing extensive degradation during the acid elution procedure.)

(d) Linkage of anti-B2M to antigenic material

The monoclonal antibody (which is usually IgG, for example IgG2) or Fab or F(ab')₂ fragment thereof in aqueous solution as obtained in (a), (b) or (c) above, is treated with 0.1 M N-ethylmaleimide (NEM) for 1 hour at room temperature to block any reactive sulphydryl groups and is then re-isolated by Sephadex gel filtration eluting with 0.05 M tris chloride. The protein is incubated at 5 mg/ml in 0.05 M tris chloride of H 7.3 with an approximately 5 molar excess of N-(m-maleimidobenzoyloxy)succinimide (MBS) for 1.5 hours at room temperature. The acylation reaction is terminated by the addition of an excess of a 20 mg/ml aqueous solution of lysine and the m-maleimidobenzoyl derivative of the antibody (MBS/anti-B2M) is separated by Sephadex G25 using phosphate-buffer saline.

The MBS/anti-B2M is reacted with a molar excess of the antigenic material at a concentration of this material of 5-10 mg/ml in phosphate-buffered saline for 5-16 hours at room temperature. The resulting combination of antigenic material/MBS/anti-B2M is then purified by gel filtration on Sephadex G200 in phosphate-buffered saline. The desired complex of antigenic material/MBS/anti-B2M is clearly separated from unreacted MBS/anti-B2M by virtue of its larger size. As an alternative, an immunosorbent purification procedure as described in Example 3 may be employed.

B2M binding capacity may be tested for by incubation with radio-iodinated B2M, the mixture being examined for the change in mobility of labelled protein, a new peak corresponding to a radio-labelled protein of appropriately higher molecular weight indicating binding of the labelled B2M.

EXAMPLE 2

PREPARATION OF ANTIGENIC MATERIAL/ANTI-B2M/B2M/HLA COMBINATION (a) Preparation of B2M-HLA Whole B2M-HLA is prepared by a method similar to that of Robb and Strominger (Journal of Biological Chemistry, 1976, 251, 5427) but using a column of mouse anti-human B2M prepared as described in Example 1, eluting with pure human B2M (prepared as described in Example 1) in phosphate buffered saline at a concentration of about 1 mg/ml. The purified B2M-HLA thus obtained is separated from the B2M by gel filtration on Sephadex G75 eluting with phosphate buffered saline.

The complex may optionally be treated with N-ethylmaleimide as described for the antibody in Example 1(a) to block sulphydryl groups.

(b) Reaction of B2M-HLA with antigenic material/anti-B2M combination

Having characterised the antigenic material/anti-B2M combination as described in Example (1) above, both by molecular weight and by its ability to react with B2M chains, the desired complex of B2M-HLA with antigenic material/anti-B2M is achieved by a simple mixing of these two materials in equivalent proportions in phosphate buffered saline followed by a brief incubation. The resulting material may be purified by gel chromatography on Sephadex G75 eluting with phosphate buffered saline or alternatively may be administered directly.

EXAMPLE 3

PREPARATION OF OVALBUMIN/ANTI-B2M

The Fab fragment of anti-B2M is prepared as described in Example 1(b). It is then treated in aqueous solution with 0.1 M N-ethyl maleimide (NEM) for 1 hour at room temperature to block any reactive sulphydryl groups and is then re-isolated by Sephadex gel filtration eluting with phosphate buffered saline. The NEM Fab is concentrated by membrane filtration to a concentration of 4.61 mg/ml (Lowry) and 1.5 ml (total protein 6.9 mg). To this solution in phosphate buffered saline is added 0.15 μl of dioxane containing 1.14 mg MBS (molar ratio: 3.63 μmol MBS/0.14 μmol protein=26.3). The mixture is maintained at room temperature for 1.5 hours and is then chromatographed on a small column (1 cm×10 cm) of Sephadex G50 in phosphate buffered saline. The NEM Fab/MBS peak emerges in the void volume and is identified by UV absorption. Protein containing fractions (about 2 ml total) are pooled and 10 mg (0.22 μmol) of crystalline ovalbumin is added and mixed to effect solution. The mixture is left overnight at room temperature and is then applied to a column (8 cm×7 cm) of Sephadex G200 in phosphate buffered saline. Two peaks are obtained of molecular weight 100,000 (ovalbumin/anti-B2M complex) and 50,000 (unreacted ovalbumin plus NEM Fab/MBS). Yields of up to 50% based on the NEM Fab starting material are obtained.

Proof of the presence of both covalently bound Fab and covalently bound ovalbumin in this complex are obtained as follows.

Radio-iodinated B2M is mixed with the complex in phosphate buffered saline, incubated for 1 hour at 37° C. and chromatographed on Sephacryl S300, all radioactivity is then eluted at a position corresponding to a molecular weight of at least 110,000 indicating binding of the B2M by the complex. Control chromatograms containing radio-iodinated B2M and irrelevant protein show B2M elution and the anticipated unbound molecular weight of about 12,000.

The presence of ovalbumin in the complex is shown by double diffusion in gels between the complex and on established rabbit anti-ovalbumin serum, or by incubating complex with radio-iodinated B2M followed by a rabbit anti-ovalbumin serum when all radio activity moves to a position on Sephacryl S300 chromatography corresponding to a molecular weight in excess of 250,000.

In a variant of the procedure described above, the reaction mixture from the NEM Fab/MBS-ovalbumin reaction is passed through a column (2×25 cm) of Sepharose 4-B2M which is then washed through with phosphate buffered saline until no further UV absorbing material emerges. The column effluent tubing is then connected to the inlet port of a 2×90 cm column of Sephacryl S300 previously equilibrated with phosphate buffered saline 0.20 ml of 9.5% v/v acetic acid is then passed through the two columns connected in tandem, followed by phosphate buffered saline until all protein and acid has emerged from the system. Two protein containing peaks of molecular weight 100,000 (complex) and 50,000 (unreacted NEM Fab/MBS) are obtained.

EXAMPLE 4

PREPARATION OF OVALBUMIN/ANTI-B2M/B2M/HLA

B2M-HLA is prepared as described in Example 2 and is incubated with ovabumin/anti-B2M prepared as described in Example 2(b) for 1 hour at 37° C.

Combination between the two complexes from ovalbumin/anti-B2M/B2M-HLA is confirmed by carrying out the reaction with radio-iodinated B2M-HLA and chromatographing the resultant reaction mixture on Sephacryl S300. All radio activity is eluted in a position corresponding to a molecular weight in excess of 150,000 in contrast to the situation with unreacted radio-iodinated B2M-HLA when the radio-activity is eluted in a position corresponding to a molecular weight of 45,000.

I claim:

1. An antigenic material in combination with a major histocompatibility complex antigen which is is itself in the form of a complex with a protein with which it is normally associated in nature or with a modified form of such protein which retains the epitope thereof intact, said antigenic material being attached to the protein of the complex through antibody to that protein.

2. An antigenic material in combination with a human lymphocyte antigen or a non-human, major hostocompatibility complex antigen which is analogous thereto, said human lymphocyte antigen or other major histocompatibility complex antigen itself being in the form of a complex with its associated B2-microglobulin protein or with a modified form of such protein which retains the epitope thereof intact and said antigenic material being attached to the B2-microglobulin of the complex through antibody thereto.

3. A combination according to claim 1 or 2, wherein the antigenic material is attached to the antibody through a linking group.

4. A combination according to claim 1 or 2, wherein the antigenic material is a bacterial antigen.

5. A combination according to claim 1 or 2, wherein the antigenic material is a viral antigen.

6. A combination according to claim 1 or 2, wherein the antigenic material is a hormone peptide.

7. A combination according to claim 1 or 2, wherein the antigenic material is attached through antibody to the protein to a major histocompatibility complex antigen-protein complex containing the protein in unmodified form.

8. A combination according to claim 1 or 2, wherein the antigenic material is attached to the protein or modified protein through a Fab or F(ab')2 fragment of antibody to the protein.

9. A combination according to claim 8, wherein the attachment is through F(ab')2.

10. A combination according to claim 2, wherein the antibody is of the IgG type.

11. A combination according to claim 3, wherein the linking group is derived from a heterobifunctional coupler.

12. A combination according to claim 11, wherein the linking group is derived from N-(m-maleimidobenzoyloxy)-succinimide.

13. A combination according to claim 11, wherein the antibody has sulphydryl groups which are blocked.

14. A combination according to claim 11, wherein the major histocompatibility complex antigen has sulphydryl groups which are blocked.

15. An immunological preparation for human or veterinary use comprising an antigenic material in combination with a major histocompatibility complex antigen which is itself in the form of a complex with a protein with which it is normally associated in nature or with a modified form of such protein which retains the epitope thereof intact, said antigenic material being attached to the protein of the complex through antibody to that protein, together with a physiologically acceptable diluent or carrier.

16. A preparation according to claim 15, being for use in humans, wherein said complex is a human lymphocyte antigen-B2-microglobulin complex.

17. A preparation according to claim 16, wherein the antigenic material is a bacterial toxin or toxoid.

18. A preparation according to claim 17, wherein the toxoid is diphtheria toxoid.

19. A preparation according to claim 16, wherein the antigenic material is an influenza virus antigen.

20. A preparation according to claim 16, wherein the antigenic material is human chorionic gonadotropin.

21. A preparation according to claim 15, being for veterinary use, wherein said complex is a major histocompatibility complex antigen-B2-microglobulin complex in which the major histocompatibility complex antigen is a non-human antigen analogous to human lymphocyte antigen.

22. A preparation according to claim 21, wherein the antigenic material is a foot and mouth disease virus antigen and the major histocompatibility complex antigen is bovine or porcine lymphocyte antigen.

23. A process for preparing a combination of an antigen with a major histocompatibility complex antigen which comprises reacting together (1) a complex of the major histocompatibility complex antigen with a protein with which it is normally associated in nature or with a modified form of such protein which retains the epitope thereof intact and (2) a combination of said antigenic material with antibody against said protein.

24. A method for the production of an immunogenic response in a mammal or bird to an antigenic material which comprises administering thereto said antigenic material in combination with a major histocompatibility complex antigen which is itself in the form of a complex with a protein with which it is normally associated in nature or with a modified form of such protein which retains the epitope thereof intact, said antigenic material being attached to the protein of the complex through antibody to that protein.

25. A method according to claim 24, wherein the major histocompatibility complex antigen is a human lymphocyte antigen or a non-human major histocompatibility complex antigen which is analogous thereto, said human lymphocyte antigen or other major histocompatibility complex antigen itself being in the form of a complex with its associated B2-microglobulin protein or with a modified form of that protein which retains the epitope thereof intact, and said antigenic material being attached to the B2-microglobulin through antibody thereto.

26. A method according to claim 24 or 25, wherein the antigenic material is a bacterial antigen.

27. A method according to claim 24 or 25, wherein the antigenic material is a viral antigen.

28. A method according to claim 24 or 25, wherein the antigenic material is a hormone peptide.

* * * * *